US006248585B1

(12) United States Patent
Berd

(10) Patent No.: US 6,248,585 B1
(45) Date of Patent: Jun. 19, 2001

(54) COMPOSITIONS FOR PRESERVING HAPTENIZED TUMOR CELLS FOR USE IN VACCINES

(75) Inventor: David Berd, Wyncote, PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 09/441,280

(22) Filed: Nov. 16, 1999

Related U.S. Application Data
(60) Provisional application No. 60/109,248, filed on Nov. 19, 1998.

(51) Int. Cl.[7] .............................. C12N 5/22; A01N 1/00; A01N 1/02; A61K 35/12
(52) U.S. Cl. .................... 435/325; 435/325; 435/405; 435/2; 435/1.1; 424/93.1
(58) Field of Search ................................ 435/405, 2, 325, 435/1.1; 424/93.1

(56) References Cited

U.S. PATENT DOCUMENTS

| | | | |
|---|---|---|---|
| 5,580,714 | 12/1996 | Polovina | 435/2 |
| 5,955,257 | * 9/1999 | Burger et al. | 435/2 |

FOREIGN PATENT DOCUMENTS

| | | | |
|---|---|---|---|
| WO 96/40173 | 12/1996 | (WO) | A61K/35/12 |
| WO 96/40866 | 12/1996 | (WO) | C12N/5/00 |
| WO 97/33975 A1 | 9/1997 | (WO) . | |
| WO 98/06822 | 2/1998 | (WO) | C12N/5/02 |
| WO 99/40925 A2 | 8/1999 | (WO) . | |
| WO 99/56773 A2 | 11/1999 | (WO) . | |

OTHER PUBLICATIONS

Berd, et al., Journal of Clinical Oncology, 15(6):2359–2370.
Cannon et al., PDA:J. Pharm. Sci. & Tech., 1995; 49:77–82.
Chang et al., Pharm. Sci., 1996; 85:129–132.
Niemeijer et al,. Ann. Allergy Asthma Immunol., 1996; 76:535–540.
Paige et al., Pharmaceutical Res., 1995; 12:1883–1888.
Muller et al, "Enhanced Antigenicity of Autologous Leukemia Cells Enriched with Cholesterylhemisuccinate." Anticancer Research, vol. 11, pp. 925–930, 1991.*
Berd et al, "Treatment of Human Melanoma with a Hapten–Modified Autologous Vaccine." Annals of the New York Academy of Science, vol. 12, No. 690, pp. 147–152, Aug. 1993.*
Berd et al, "Induction of delayed–type hypersensitivity to ovarian cancer cells after treatment with an autologous, hapten–modified vaccine." Proceedings of the American Association for Cancer Research, vol. 39, p. 356, Mar. 1998.*

* cited by examiner

Primary Examiner—Anthony C. Caputa
Assistant Examiner—Karen A. Canella
(74) Attorney, Agent, or Firm—Darby & Darby

(57) ABSTRACT

A composition comprising an isotonic, buffered aqueous medium containing an optimized concentration of human serum albumin has been found to stabilize irradiated, haptenized tumor cells stored for some period of time after haptenization. In specific embodiments, the viability of the haptenized tumor cells stored in a composition of the invention ranged from about 60% to about 100% greater than the cell viability of cells stored in a prior art solution. In a specific embodiment, 1% human serum albumin in Hank's Buffered Salt Solution was found to stabilize haptenized melanoma cells. Methods of storing haptenized tumor cells and vaccine preparations are also provided.

18 Claims, No Drawings

COMPOSITIONS FOR PRESERVING HAPTENIZED TUMOR CELLS FOR USE IN VACCINES

This application claims the benefit of the filing date of Provisional Patent Application Serial No. 60,109,248, filed Nov. 19, 1998, the disclosure of which is incorporated herein, by reference, in its entirety.

FIELD OF THE INVENTION

The invention relates to compositions comprising a haptenized tumor cell and human serum albumin (HSA) effective to stabilize the haptenized tumor cells in an aqueous buffer.

BACKGROUND OF THE INVENTION

In blood transfusion, bone marrow transplantation, or other cell cultures ex vivo, one of the principal problems encountered is that of the preservation of cells. It is critical to be able to preserve cells, under good conditions of viability, for time periods compatible with clinical production and storage, and to make it possible to analyze cell preparations. The most commonly used method of long-term preservation of cells is to freeze and thaw the material. However, during the freezing of cells, loss of viability may occur. This problem can be even more complex when the cells have been modified or altered prior to preservation, and when the cells are obtained by proteolytic digestion of a tissue or tumor specimen. Furthermore, preservation of cells on ice (about 0° C.), refrigerated (about 4° C.), or at room temperature, prior to use, is also difficult.

Human Serum Albumin

Human serum albumin is a non-glycosylated monomeric protein consisting of 585 amino acid residues, with a molecular weight of 66 kD. Its globular structure is maintained by 17 disulfide bridges, which create a sequential series of 9 double loops (Brown, "Albumin structure, function and uses", Rosenoer, V. M. et al. (eds.), Pergamon Press, Oxford, pp. 27–51, 1977). The genes encoding for HSA are known to be highly polymorphic, and more than 30 apparently different genetic variants have been identified by electrophoretic analysis (Weitkamp, et al., Ann. Hum. Genet., 37:219–226, 1973). The HSA gene comprises 15 exons and 14 introns comprising 16,961 nucleotides, from the supposed "capping" site up to the first site of addition of poly(A).

Human albumin is synthesized in the hepatocytes of the liver, and then secreted into the peripheral blood. In a first instance, this synthesis leads to a precursor, prepro-HSA, which contains a signal sequence of 18 amino acids directing the nascent polypeptide in the secretory pathway.

HSA is the most abundant blood protein, with a concentration of about 40 grams per liter of serum. Therefore, there are about 160 grams of circulating albumin in the human body at any one time. The most important role of HSA is to maintain a normal osmolarity of the blood. It also has an exceptional binding capacity for various substances, and plays a role both in the endogenous transport of hydrophobic molecules, such as steroids and bile salts, and in that of the transport of different therapeutic substances to their respective sites of action. HSA has been recently been implicated in the breakdown of the prostaglandins. Furthermore, HSA has previously been shown to stabilize solutions of proteins, including protein antigens, and small organic molecules such as hemin (Paige, A. G. et al., Pharmaceutical Res., 12:1883–1888, 1995; Chang, A.- C. and R. K. Gupta, J., Pharm. Sci., 85:129–132, 1996; Niemeijer, N. R. et al., Ann. Allergy Asthma Immunol., 76:535–540, 1996; and Cannon, J. B. et al., PDA:J. Pharm. Sci. & Tech., 49:77–82, 1995).

Haptenized Tumor Cell Vaccines

An autologous whole-cell vaccine modified with the hapten dinitrophenyl (DNP) has been shown to produce inflammatory responses in metastatic sites of melanoma patients. Adjuvant therapy with DNP-modified vaccine produces markedly higher post-surgical survival rates than those reported after surgery alone. Previous work suggested that this vaccine might have a cell integrity duration of less than four hours after hapten modification. Intact or viable cells are preferred for the vaccine.

U.S. Pat. No. 5,290,551, to David Berd, discloses and claims vaccine compositions comprising haptenized melanoma cells. Melanoma patients who were treated with these cells developed a strong immune response. This response can be detected in a delayed-type hypersensitivity (DTH) response to haptenized and non-haptenized tumor cells. More importantly, the immune response resulted in increased survival rates of melanoma patients.

Haptenized tumor cell vaccines have also been described for other types of cancers, including lung cancer, breast cancer, colon cancer, pancreatic cancer, ovarian cancer, and leukemia (see U.S. patent application Ser. No. 08/203,004, filed Feb. 28, 1994; International Patent Application No. PCT/US96/09511; U.S. patent application Ser. No. 08/899, 905, filed Jul. 24, 1997).

Cell stabilization and preservation is an important problem in the storage of haptenized tumor cells for administration. Generally, the cells are recovered from tumors, suspended in a cryopreservation medium and frozen until used for the vaccine preparation. When needed, the cells are thawed, haptenized, and then stored for about 1 to about 24 hours, usually about 1 to about 2 hours, at temperatures ranging from about 0° C. (on ice) to room temperature. Under prior art conditions of 0.1% HSA in Hank's Balanced Salt Solution (HBSS) (e.g., see application Ser. No. 08/899, 905), the cell viability decreases by more than 50% (i.e. viability is less than 50%) after 18 hours. Thus, there is a need in the art for an effective formulation for storing and preserving the cells after haptenization and prior to delivery as a vaccine. There is a further need for a storage solution that can also serve as a safe delivery vehicle.

The citation of any reference herein should not be construed as an admission that such a reference is available as "Prior Art" to the instant application.

SUMMARY OF THE INVENTION

The present invention advantageously provides a formulation for the preservation and/or storage of haptenized tumor cells for use in anti-tumor vaccines. Thus, in a first embodiment, the invention provides a composition comprising a haptenized tumor cell and a concentration of human serum albumin (HSA) effective to stabilize the haptenized tumor cells in solution from the time of haptenization until administration to the patient. Haptenized tumor cell viability in the formulation of the invention is greater than the viability of the same kind, number, and concentration of haptenized tumor cells in a control medium comprising 0.1% HSA (w/v), over the same period of time. Preferably, cell viability in a formulation of the invention is at least 50% after 18 hours. In a specific embodiment, in which the tumor cells are human tumor cells, the serum albumin is HSA. Preferably, the concentration of HSA is at least about 0.25%. More preferably, the concentration of HSA is at least about 0.5%. Most preferably, the concentration is at least about 1%. HSA can be purified from natural sources, or preferably, obtained by genetic engineering.

The advantage of such a formulation stems from the fact that the haptenized tumor cells and HSA solution are available for administration immediately after haptenization without any further manipulation being necessary. It then becomes possible to carry out the haptenization and storage conditions in a suitable laboratory for subsequent delivery to the clinic. Thereby, the time between storage and use would be reduced, which would also increase the chances for maintaining sterility.

The invention further provides a method for preparing haptenized tumor cells for use in a vaccine. The method comprises suspending the haptenized tumor cells in an aqueous medium comprising a concentration of HSA effective to stabilize the haptenized tumor cells, wherein the haptenized tumor cell viability over time is greater than the viability of the same kind, number, and concentration of haptenized tumor cells stored in a control solution comprising 0.1% HSA over the same period of time. Preferably, the aqueous medium comprises HSA and HBSS. In still a further embodiment, the suspended cells can be mixed with an adjuvant to form a vaccine.

The present invention will be further explained in the Detailed Description.

DETAILED DESCRIPTION OF THE INVENTION

The present invention advantageously provides a new type of medium which stabilizes haptenized tumor cells stored at between about 0° C. (on ice) and 20° C. (at room temperature) after haptenization, and prior to delivery to the patient. The formulation for the preservation and/or storage of haptenized tumor cells comprises an optimized concentration of HSA. The optimized concentration of HSA preserves cell viability, as determined by Trypan Blue exclusion, to a greater extent than that of a control solution containing 0.1% HSA. Preferably, the concentration of HSA preserves greater than about 50% cell viability after 18 hours; more preferably, cell viability is at least about 70% after 18 hours. A preferred HSA concentration is at least about 0.25%; a more preferred concentration is at least about 0.5%. In a specific embodiment, the concentration of HSA is about 1% (w/v).

The various aspects of the invention will be set forth in greater detail in the following sections, directed to suitable media and formulations for preserving haptenized tumor cells. This organization into various sections is intended to facilitate understanding of the invention, and is in no way intended to be limiting thereof.

Definitions

The following defined terms are used throughout the present specification, and should be helpful in understanding the scope and practice of the present invention.

In a specific embodiment, the term "about" or "approximately" means within 20%, preferably within 10%, and more preferably within 5% of a given value or range.

A "formulation" refers to an aqueous medium or solution for the preservation of haptenized tumor cells, which is preferably directly injectable into an organism. The aqueous buffer will include salts or sugars, or both, at about an isotonic concentration.

"Human serum albumin" or "HSA" refers to a non-glycosylated monomeric protein consisting of 585 amino acid residues, with a molecular weight of 66 kD. Its globular structure is maintained by 17 disulphide bridges, which create a sequential series of 9 double loops (Brown, "Albumin structure, function and uses", Rosenoer, V. M. et al. (eds.), Pergamon Press:Oxford, pp. 27–51, 1977). The genes encoding HSA are known to be highly polymorphic, and more than 30 apparently different genetic variants have been identified by electrophoretic analysis under varied conditions (Weitkamp, L. R. et al., Ann. Hum. Genet., 37:219–226, 1973). The HSA gene comprises 15 exons and 14 introns comprising 16,961 nucleotides, from the putative mRNA "capping" site up to the first site of addition of poly(A). HSA may also be called human plasma albumin.

The phrase "pharmaceutically acceptable" refers to molecular entities, at particular concentrations, and compositions, that are physiologically tolerable and do not typically produce an allergic or similar untoward reaction, such as gastric upset, fever, dizziness and the like, when administered to a human or non-human animal. Preferably, as used herein, the term "pharmaceutically acceptable" means approved by a regulatory agency of the Federal or a state government, or listed in the U.S. Pharmacopoeia or other generally recognized pharmacopoeia for use in humans or non-human animals.

A "subject" is a human or a non-human animal who may receive haptenized tumor cells formulated in a composition of the invention. Non-human animals include domesticated pets, such as cats and dogs; farm animals, such as horses, cows, pigs, sheep, and goats; laboratory animals, such as mice, rats, guinea pigs, and rabbits; etc.

Human Serum Albumin

The HSA used within the framework of the present invention may be either of natural origin (purified HSA) or of the recombinant origin (rHSA). Naturally, for delivery of a formulation in vivo, it is preferable to use an autologous serum albumin. Thus, for human therapy, HSA is desirable and preferred. Thus, although the present invention described predominantly relates to HSA formulations in the context of human haptenized tumor cell vaccines, the skilled person can immediately appreciate that any serum albumin can be used in the practice of this invention, and, more particularly, any autologous serum albumin can be used in connection with haptenized tumor cell vaccine for cancer treatment in any non-human animal as well.

Advantageously, a recombinant or natural HSA is used which meets certain quality criteria (e.g., homogenetic, purity, stability). Thus, the pharmacopoeias set a number of parameters for the albumin solutions, namely a pH value, a protein content, a polymer and aggregate content, an alkaline phosphatase content, and a certain protein composition. It imposes, furthermore, a certain absorbance, the compliance with tests for sterility, pyrogens, and toxicity (see "Albumini humai solutio", European Pharmacocpoeia (1984), 255). The use of an albumin composition corresponding to these criteria, although not essential, is particularly preferred.

Advantageously, the compositions according to the invention comprise purified HSA or recombinant HSA, preferably produced in a eukaryotic host. In addition, the term HSA comprises, for the purpose of the invention, any natural variant of human albumin, resulting from the polymorphism of this protein. It is also possible to use an HSA equivalent, that is to say, any HSA derivative conserving the properties of HSA. These derivatives may be especially amino- (N-) terminal fragments of HSA.

Purification of Natural HSA

Natural HSA is generally produced by purification from biological material of human origin. In particular, it is obtained by conventional techniques for fractionation of plasma obtained from blood donations (Cohn et al., 1946. J. Am. Chem. Soc., 68:459 pp.), or by extraction from the human placenta, according to the technique described by J. Liautraud et al. (1973, 13$^{th}$ International IABS Conference, Budapest; A: "Purification of proteins. Development of biological standard", Karger (ed.), Bale, 27:107 pp). Most particularly, a commercial albumin may be used. In a specific embodiment, a Human Serum Albumin Solution (American Red Cross), which is a 25% HSA solution, is used.

Recombinant Production of HSA

The development of genetic engineering and new extraction and purification techniques has opened the possibility of obtaining, at a lower cost, improved products of higher purity, of greater stability, and without risk of contamination (of, for example, hepatitis B, hepatitis C, HIV, or infectious prions). Given the importance of the HSA market, the possibility of producing this protein by a recombinant route has been widely studied. Thus, numerous expression systems have been studied for the preparation of the recombinant HSA.

More particularly, as regards the bacterial hosts, genetic engineering can be accomplished in a bacterium, for example, *Escherichia coli*, as a host organism. European patents EP 236 210, EP 200 590, or EP 198 745 describe processes for the production of HSA in *E. coli* using different expression vectors, different transcriptional promoters, and different secretory signals. Subsequently, secretion of HSA in *Bacillus subtilis* was also carried out (Saunders et al., J. Bacteriol., 169:2917, 1987).

As to the eukaryotic hosts, processes for the production of HSA have been developed using yeast as a host organism. Thus, it has been possible to demonstrate the production of HSA under the control of the chelatin promoter in *Saccharomyces cerevisiae* (Etcheverry et al., Bio/Technology, 4:726, 1986). The production of HSA has also been mentioned in the brewery yeast during the manufacture of beer, using a post-fermentative process (EP 201 239). Most recently, patent application EP 361 991 describes a particularly efficient system using the yeast Kluyveromyces as a host organism, transformed with vectors derived from the plasmid pKD1. With this system, particularly high levels of HSA were secreted into the culture medium, and could be obtained. The production of recombinant HSA has also been described in *Pichia pastoris*, (EP 344 450). In addition, the purification of HSA has been described (EP 319 067). RECOMBUMIN™ is a yeast-derived, recombinant human albumin that is structurally identical to plasma-derived HSA, manufactured by Centeon (King of Prussia, Pa., USA).

Various patents and scientific publications describe methods for expressing a heterologous gene, particularly HSA, in a transgenic animal, optimally in the mammary gland of a ruminant mammal. Such technology is useful for producing a heterologous protein in the milk of the mammal. Examples of production of human serum albumin in transgenic animals include U.S. Pat. No. 5,780,009, issued Jul. 14, 1998, to Karatzas et al., describing direct gene transfer into the ruminant mammary gland. U.S. Pat. No. 4,873,316, issued Oct. 10, 1989 to Meade et al., directed to isolation of exogenous recombinant proteins from the milk of transgenic mammals, provides an expression system comprising the mammal's casein promoter, which, when transgenically incorporated into a mammal, permits the female of that mammal species to produce the desired recombinant protein in or along with its milk. A preferred construct for transgenic expression of HSA is described in U.S. Pat. No. 5,648,243, issued Jul. 15, 1997, to Hurwitz et al., directed to a HSA expression construct, the disclosure of which is incorporated herein by reference in its entirety. As disclosed in Hurwitz et al., efficient expression of HSA is achieved when the human serum albumin sequence comprises at least one, but not all, of the introns in the naturally occurring gene encoding for the HSA protein; preferably the DNA constructs comprise a 5' regulatory sequence which directs the expression and secretion of HSA protein in the milk of a transgenic animal. These patents refer to additional references from the scientific and patent literature for transgenic expression, particularly of HSA. Each of them is incorporated herein by reference it its entirety.

HSA Formulations

The formulations according to the invention may be prepared in various ways. The different components may be mixed together, and then added to haptenized tumor cells. It is also possible to mix one or several of the components with the haptenized tumor cells and then to add the remaining component(s). The preparation of the formulation and its addition of the haptenized tumor cells are preferably performed under sterile conditions.

The respective proportions of the components of the media according to the invention may be adapted by persons skilled in the art. As illustrated in the Examples, the proportions may be modified although certain concentration ranges are preferred.

Generally, HSA will be added to an appropriate buffered cell culture medium. In its essence, a buffered cell culture medium is an isotonic buffered aqueous solution, such as phosphate buffered saline (PBS), Tris-buffered saline, or HEPES buffered saline. In a preferred embodiment, the medium is plain Hank's medium (not containing phenol red), e.g., as sold commercially by Sigma Chemical Co. (St. Louis, Mo., USA). Other tissue culture media can also be used, including basal medium Eagle (with either Earle's or Hank's salts), Dulbecco's modified, Eagle's medium (DMEM), Iscove's modified Dulbecco's medium (IMDM), Medium 199, Minimal Essential Medium (MEM) Eagle (with Earle's or Hank's salts), RPMI, Dulbecco's phosphate buffered salts, Earle's balanced salts (EBSS), and Hank's Balanced Salts (HBSS). These media can be supplemented, e.g., with glucose, Ham's nutrients, or HEPES. Other components, such as sodium bicarbonate and L-glutamine, can be specifically included or omitted. Media, salts, and other reagents can be purchased from numerous sources, including Sigma, Gibco, BRL, Mediatech, and other companies.

As used herein, the term "control solution" generally describes a composition containing 0.1% HSA (w/v). More preferably, a control solution describes a composition containing 0.1% HSA (w/v), which in essentially all other aspects than HSA concentration, e.g., choice of buffered culture medium and additional components, is similar to that of a composition optimized for cell storage according to the invention. Most preferably, the control solution is 0.1% HSA in HBSS.

As noted above, and demonstrated in the Examples, infra, it has been unexpectedly discovered that an optimized concentration of HSA in a buffered cultured medium, preferably HBSS, greatly increases cell viability over time. This is especially advantageous for the irradiated, haptenized tumor cells for use in vaccine preparation. Accordingly, depending on the specific culture medium and tumor cells to be stored, one of ordinary skill in the art can test for the optimum HSA concentration for such medium and cells, as exemplified infra. Such a concentration can be one that yields an increase in cell viability relative to a control 0.1% HSA medium solution for storage of irradiated, haptenized melanoma tumor cells. Preferably the increase in viability is statistically significant. In a specific embodiment, cell viability in an HSA formulation of the invention is about 70%, while cell viability of cells stored in a control solution is less than about 50% (in one example, 40–50%). Thus, cell viability can be improved by about 60% to about 100% using an HSA formulation of the invention relative to a control 0.1% HSA formulation.

Generally, the HSA formulation of the invention is made by adding HSA powder or solution to the selected culture medium/balanced salt solution, to achieve the desired final concentration. In a specific embodiment, the final concentration of HSA is about 1.0% in a Hank's culture medium. However, an unexpected improvement in cell viability can be achieved using at least about 0.25% HSA. In a specific embodiment, cell viability is improved using 0.3% HSA as compared to 0.1% HSA. An even greater improvement is possible using at least about 0.5% HSA.

Although in a specific embodiment, the most effective HSA concentration was at least about 1.0%, higher concentrations are possible. Upper limits to the concentration are determined by the need to avoid contaminants that may be present in naturally-derived HSA, or, alternatively, to avoid allergic reaction to recombinant HSA. Preferably, the concentration of HSA in a formulation of the invention is no more than about 10%. More preferably, the concentration is less than or equal to about 5% and, most preferably still less than or equal to about 2%.

In addition, a composition or formulation of the invention may contain components in addition to HSA to further stabilize the haptenized tumor cells. Examples of such components include, but are not limited to, carbohydrates and sugars such as dextrose, sucrose, glucose, and the like, e.g., at a 5% concentration; medium to long chain polyols such as glycerol, polyethylene glycol, and the like, e.g., at 10% concentration; other proteins; amino acids; nucleic acids; chelators; proteolysis inhibitors; preservatives; and other components. Preferably, any such constituent of a composition of the invention is pharmaceutically acceptable.

Haptenized Tumor Cells

The present invention is directed for use in the preparation of haptenized tumor cell vaccines for treating cancer, including metastatic and primary cancers. Cancers treatable with the present invention include solid tumors, including carcinomas; and non-solid tumors, including hematologic malignancies. Examples of solid tumors that can be treated according to the invention include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. Hematologic malignancies include leukemias, lymphomas, and multiple myelomas. The following are non-limiting preferred examples of the cancers treatable with the composition and methods of the present invention: melanoma, including stage-4 melanoma; ovarian, including advanced ovarian; leukemia, including and not limited to acute myelogenous leukemia; colon, including colon metastasized to liver; rectal, colorectal, breast, lung, kidney, and prostate cancers.

Tumor Cells

The compositions of the present invention are prepared from tumor cells, e.g., obtained from tumors surgically resected in the course of a treatment for a cancer as described above. The tumor cells of the present invention may be live or live, attenuated cells. Tumor cells less capable of growing and dividing after administration into the subject, such that they are substantially in a state of no growth, are preferred for use in the present invention. It is to be understood that "cells in a state of no growth" means live cells that will not divide in vivo. Conventional methods of suspending cells in a state of no growth are known to skilled artisans and may be useful in the present invention. For example, cells may be irradiated prior to use such that they do not multiply. Tumor cells may be irradiated to receive a dose of 2500 cGy to prevent the cells from multiplying after administration. Alternatively, haptenization itself can result in a state of no growth.

The tumor cells are preferably of the same type as, most preferably syngeneic (e.g., autologous or tissue-type matched) to, the cancer which is to be treated. For purposes of the present invention, syngeneic refers to tumor cells that are closely enough related genetically that the immune system of the intended recipient will recognize the cells as "self", e.g., the cells express the same or almost the same complement of HLA molecules. Another term for this is "tissue-type matched." For example, genetic identity may be determined with respect to antigens or immunological reactions, and any other methods known in the art. Preferably the cells originate from the type of cancer which is to be treated, and more preferably, from the same patient who is to be treated. The tumor cells can be, although not limited to, autologous cells dissociated from biopsy or surgical resection specimens, or from tissue culture of such cells. Nonetheless, allogeneic cells and stem cells are also within the scope of the present invention.

Hapten

The tumor cells are haptenized. For purposes of the present invention, virtually any small protein or other small molecule that fails to induce an immune response when administered alone, may function as a hapten. A variety of haptens of quite different chemical structure have been shown to induce similar types of immune responses: TNP (Kempkes et al., J. Immunol., 147:2467, 1991); phosphorylcholine (Jang et al., Eur. J. Immunol., 21:1303, 1991); nickel (Pistoor et al., J. Invest. Dermatol., 105:92, 1995); arsenate—Nalefski and Rao, J. Immunol., 150:3806, 1993). Conjugation of a hapten to a cell to elicit an immune response may preferably be accomplished by conjugation via $\epsilon$-amino groups of lysine or —COOH groups. This group of haptens include a number of chemically diverse compounds: dinitrophenyl, trinitrophenyl, N-iodoacetyl-N'-(5-sulfonic 1-naphthyl) ethylene diamine, trinitrobenzenesulfonic acid, dinitrobenzene sulfonic acid, fluorescein isothiocyanate, arsenic acid benzene isothiocyanate, and dinitrobenzene-S-mustard (Nahas and Leskowitz, Cellular Immunol., 54:241, 1980). Once armed with the present disclosure, skilled artisans would be able to choose haptens for use in the present invention.

Isolation and Haptenization of Tumor Cells

The tumor cells for use in the present invention may be prepared as follows. Tumors are processed as described by Berd et al (Cancer Res., 46:2572, 1986; see also U.S. Pat. No. 5,290,551; U.S. patent applications Ser. No. 08/203,004, No. 08/475,016, and No. 08/899,905). The cells are extracted by dissociation, such as by enzymatic dissociation with collagenase and DNase, or by mechanical dissociation such as with a blender, teasing with tweezers, mortar and pestle, cutting into small pieces using a scalpel blade, and the like. Mechanically dissociated cells can be further treated with enzymes as set forth above to prepare a single cell suspension.

The dissociated cells may be stored frozen in a freezing medium (e.g., prepared from a sterile-filtered solution of 50 ml Human Serum Albumin [American Red Cross] added to 450 ml of RPMI 1640 [Mediatech] supplemented with L-glutamine and brought to an appropriate pH with NaOH), such as in a controlled rate freezer or in liquid nitrogen until needed. The cells are ready for use upon thawing. Preferably, the cells are thawed shortly before haptenization. Optionally, the cells may be washed, and irradiated to receive a dose of about 2500 cGy. They may be washed again and then suspended in HBSS without phenol red.

Modification of the prepared cells with DNP or another hapten may be performed by known methods, e.g. by the method of Miller and Clanian (J. Immunol., 117:151, 1976), incorporated herein by reference in its entirety, which involves a 30 minute incubation of tumor cells with DNFB under sterile conditions, followed by washing with sterile saline or Hanks/HSA.

Vaccine Preparations

The compositions of the invention may be administered in a mixture with a pharmaceutically-acceptable carrier, selected with regard to the intended route of administration and standard pharmaceutical practice. Dosages may be set with regard to weight and clinical condition of the patient. The proportional ratio of active ingredient to carrier naturally depends on the chemical nature, solubility, and stability of the compositions, as well as the dosage contemplated. The amounts to be used of the tumor cells of the invention depend on such factors as the affinity of the compound for cancerous cells, the amount of cancerous cells present and the solubility of the composition. The compounds of the present invention may be administered by any suitable route, including inoculation and injection, for example, intradermal, intravenous, intraperitoneal, intramuscular, and subcutaneous.

In a preferred embodiment of the invention, the composition comprises a vaccine comprising about $1\times10^6$ to about $25\times10^6$, more preferably about $2.5\times10^6$ to about $7.5\times10^6$, live, irradiated, tumor cells suspended in a pharmaceutically acceptable carrier or diluent, such as, but not limited to, Hanks solution, saline, phosphate-buffered saline, and water. The composition may be administered by intradermal injection into 3 contiguous sites per administration on the upper arms or legs, excluding limbs ipsilateral to a lymph node dissection.

Adjuvant

In preferred embodiment, a tumor cell composition may be administered with an immunological adjuvant. While the commercial availability of pharmaceutically acceptable adjuvants is limited, representative examples of adjuvants include Bacille Calmette-Guerin, BCG, or the synthetic adjuvant, QS-21 comprising a homogeneous saponin purified from the bark of *Quillaja saponaria*, *Corynebacterium parvum*, [McCune et al., *Cancer* 1979 43:1619], and IL-12.

It will be understood that the adjuvant is subject to optimization. In other words, the skilled artisan can engage in no more than routine experimentation and determine the best adjuvant to use.

Immunostimulants and Combination Therapies

The haptenized tumor cell compositions may be co-administered with other compounds including but not limited to cytokines such as interleukin-2, interleukin-4, gamma interferon, interleukin-12, GM-CSF. The tumor cells and extracts of the invention may also be used in conjunction with other cancer treatments including but not limited to chemotherapy, radiation, antibodies, antisense oligonucleotides, and gene therapy.

EXAMPLES

The following example is illustrative of the invention, but not limiting thereof.

Example 1

Stability of Hapten-Modified Autologous Melanoma Cell Vaccine

This example evaluates cell stability and viability after hapten-modification of the autologous melanoma cell vaccine. The data can be used to establish vaccine storage time and conditions prior to use.

Methods and Results

The presence of HSA in solution interferes with the DNP-modification process. Therefore, exposing the tumor cells to 1.0% HSA prior to DNP-modification would have required one or two extra washes to get rid of HSA. To avoid the extra washes, the cells were processed under standard conditions in 0.1% HSA until after the DNP-modification had been completed.

Several tumor samples showed a large loss of live tumor cells after DNP-modification, so that the baseline (time 0) cell counts were too low to determine shelf life. Therefore, an additional three samples were studied so that there would be an adequate number of analyzable samples.

Cells were prepared and haptenized with DNP as described previously (U.S. Pat. No. 5,290,551; U.S. patent applications Ser. No. 08/203,004; No. 08/475,016; and No. 08/899,905). After haptenization and washing, the cells were suspended in HBSS supplemented with 0.1% (standard), 0.3%, or 1% HSA (American Red Cross) and stored at 4° C.

Cell viability was evaluated at 4, 8, and 18 hours after DNP treatment. The data are shown in Table 1. Viability after 18 hours of cells stored in 0.1% HSA ranged from 11% to 89%. The mean was 48%. Cells stored in 0.3% HSA showed greater viability after 18 hours, with a range from 14% to 91%, and a mean of 56%. In 1.0% HSA, cell viability after 18 hours ranged from 31% to greater than 100% (relative to control), with a mean of 69%.

TABLE 1

Stability of Haptenized Tumor Cells

| Albumin Conc. | Patient | Post-RT[3] | Post-DNP[4] | 4 hours | 8 hours | 18 hours | % Viability[2] 18 hours/ Post-DNP |
|---|---|---|---|---|---|---|---|
| 0.1% | 1 | 20.9 | 17.3 | 12.2 | 20.4 | 15.4 | 89% |
|  | 2 | 9.4 | 6.0 | 1.8 | 2.2 | 2 | 33% |
|  | 3 | 22.3 | 19.1 | 12.2 | 10.4 | 12.1 | 63% |
|  | 4 | 3.0 | 1.0 | 0.3 | 0.5 | 0.5 | 51% |
|  | 5 | 14.9 | 10.6 | 6.1 | 3.7 | 1.2 | 11% |
|  | 6 | 29.7 | 23.0 | 10.2 | 6.5 | 5.5 | 24% |
|  | 7 | 19.9 | 17.9 | 10 | 17 | 15.3 | 85% |
|  | 8 | 15.1 | 3.9 | 0.6 | 0.9 | 0.6 | 16% |
|  | 9 | 9.1 | 4.9 | 1.2 | 1.1 | 1 | 20% |
|  | 10 | 17.6 | 14.3 | 7.2 | 4.8 | 7.8 | 55% |
|  | 11 | 16.9 | 7.6 | 2.6 | 3.6 | 3.5 | 46% |
|  | 12 | 14.8 | 8.6 | 4.5 | 4.3 | 4.8 | 56% |
|  | 13 | 31.6 | 25.9 | 17 | 18.4 | 18.6 | 72% |
| 0.3% | 1 | 20.9 | 17.3 | 13.4 | 17.8 | 11.2 | 65% |
|  | 2 | 9.4 | 6.0 | 6.4 | 3 | 2.8 | 46% |
|  | 3 | 22.3 | 19.1 | 16.9 | 13.6 | 16.8 | 88% |
|  | 4 | 3.0 | 1.0 | 1.3 | 1.3 | 0.8 | 81% |
|  | 5 | 14.9 | 10.6 | 8 | 2.8 | 2.4 | 23% |
|  | 6 | 29.7 | 23.0 | 19.2 | 16.2 | 9.1 | 40% |
|  | 7 | 19.9 | 17.9 | 16.7 | 15.2 | 16.8 | 94% |
|  | 8 | 15.1 | 3.9 | 1.1 | 1.1 | 0.8 | 21% |
|  | 9 | 9.1 | 4.9 | 1.6 | 1.5 | 1.5 | 30% |
|  | 10 | 17.6 | 14.3 | 10.4 | 5.8 | 14 | 98% |
|  | 11 | 16.9 | 7.6 | 5 | 1.3 | 3 | 39% |
|  | 12 | 14.8 | 8.6 | 7.1 | 4.2 | 1.2 | 14% |
|  | 13 | 31.6 | 25.9 | 19.4 | 20.6 | 23.6 | 91% |
| 1% | 1 | 20.9 | 17.3 | 13.2 | 12.6 | 12.6 | 73% |
|  | 2 | 9.4 | 6.0 | 3.4 | 2.6 | 2.6 | 43% |
|  | 3 | 22.3 | 19.1 | 17 | 13.2 | 17.2 | 90% |
|  | 4 | 3.0 | 1.0 | 0.8 | 0.8 | 0.2 | 20% |
|  | 5 | 14.9 | 10.6 | 6.2 | 2 | 3.4 | 32% |
|  | 6 | 29.7 | 23.0 | 14.9 | 10.6 | 18.5 | 80% |
|  | 7 | 19.9 | 17.9 | 18.6 | 19.2 | 18 | 101% |
|  | 8 | 15.1 | 3.9 | 2.6 | 1.8 | 1.2 | 31% |
|  | 9 | 9.1 | 4.9 | 2.4 | 1.3 | 1.8 | 36% |
|  | 10 | 17.6 | 14.3 | 11.2 | 6.6 | 16.2 | 113% |
|  | 11 | 16.9 | 7.6 | 6.6 | 4.2 | 8.2 | 108% |
|  | 12 | 14.8 | 8.6 | 6.2 | 3.9 | 6.3 | 73% |
|  | 13 | 31.6 | 25.9 | 20.8 | 24.2 | 24 | 93% |

[1]Number of tumor cells (TC) × $10^{-6}$

[2]$\dfrac{\text{No. of TC after 18 hours}}{\text{No. of TC Post-DNP}} \times 100$

[3]Post-RT = after radiation treatment

[4]Post-DNP = after haptenization with DNP

Discussion

The 18 hour recovery of live tumor cells was higher in 1.0% HSA (mean=69±9%) than 0.1% (mean=48±7%); in 0.3% HSA, the result was intermediate (mean=56±9%). The statistical analysis indicates that the difference between 1.0% and 0.1% was statistically significant (p value less than 0.04).

There was an increased number of live tumor cells in 1.0% HSA as compared to 0.1% HSA. It was clear that the major losses of live tumor cells came after irradiation and DNP-modification. With some samples there was a further loss after 4 hours incubation, but minimal additional loss between 4 and 18 hours.

The data shows that preservation of live tumor cells after DNP-modification was higher when the cells were processed in a higher HSA concentration following DNP-modification. Specifically, 1.0% HSA was superior to 0.1% HSA; 0.3% HSA was intermediate. In the effective concentration of HSA, the completed vaccine appears to be stable for at least 18 hours, as measured by retention of live (i.e., Trypan-blue-excluding) tumor cells.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all weight or mass values, viability values, cell counts, and other quantitative values are to some degree approximate, and are provided for purposes of description.

Patents, patent applications, and publications are cited throughout this application, the disclosures of which are incorporated herein by reference in their entireties.

What is claimed is:

1. A composition comprising stabilized haptenized tumor cells and cell culture medium containing a concentration of human serum albumin (HSA) effective to stabilize the haptenized tumor cells, wherein the haptenized tumor cell viability over time is greater than the viability of the same kind, number, and concentration of haptenized tumor cells stored in the control cell culture medium containing 0.1% HSA over the same period of time.

2. The composition of claim 1, wherein the stabilized haptenized tumor cell viability is at least 50% after 18 hours.

3. The composition of claim 1, wherein the stabilized haptenized tumor cell viability is at least about 70% after 18 hours.

4. The composition of claim 1, wherein the stabilized haptenized tumor cell viability is increased by about 60% to about 100% greater than the viability in the control medium.

5. The composition of claim 1, wherein the cell culture medium is Hank's Balanced Salt Solution.

6. The composition according to claim 5, wherein the concentration of HSA is about 1%.

7. The composition according to claim 1, wherein the haptenized tumor cells are selected from the group consisting of haptenized colorectal cancer cells, haptenized kidney cancer cells, haptenized breast cancer cells, and haptenized leukemia cells.

8. The composition according to claim 1, wherein the haptenized tumor cells are haptenized melanoma cells.

9. The composition according to claim 1, wherein the haptenized tumor cells are haptenized ovarian cancer cells.

10. A composition comprising haptenized melanoma cells suspended in Hank's Balanced Salt Solution containing about 1% human serum albumin.

11. A method for preparing haptenized tumor cells for use in a vaccine comprising suspending the haptenized tumor cells in a cell culture medium comprising a concentration of human serum albumin effective to stabilize the haptenized tumor cells, wherein the haptenized tumor cell viability over time is greater than the viability of the same kind, number, and concentration of haptenized tumor cells, stored in the control cell culture medium containing 0.1% HSA over the same period of time.

12. The method according to claim 11, wherein the haptenized tumor cells are selected from the group consisting of haptenized colorectal cancer cells, haptenized kidney cancer cells, haptenized breast cancer cells, and haptenized leukemia cells.

13. The method according to claim 11, wherein the haptenized tumor cells are haptenized melanoma cells.

14. The method according to claim 11, wherein the haptenized tumor cells are haptenized ovarian cancer cells.

15. The method according to claim 11, wherein the cell culture medium is Hank's Balanced Salt Solution.

16. The method according to claim 15, wherein the concentration of human serum albumin is about 1%.

17. The method according to claim 11, further comprising mixing the cell culture medium containing the haptenized tumor cells with an adjuvant.

18. The method according to claim 17, wherein the adjuvant is selected from the group consisting of BCG and QS-21.

* * * * *